US011135189B2

(12) United States Patent
Sac-Epee et al.

(10) Patent No.: US 11,135,189 B2
(45) Date of Patent: Oct. 5, 2021

(54) VISCOELASTIC SOLUTION AND USE THEREOF IN RHUMATOLOGY

(71) Applicant: LABORATOIRE DE RHUMATOLOGIE APPLIQUEE, Lyons (FR)

(72) Inventors: Patrick Sac-Epee, Marcilly d'Azergues (FR); Alain Schouft, Lyons (FR); Thierry Conrozier, Belfort (FR)

(73) Assignee: LABORATOIRE DE RHUMATOLOGIE APPLIQUEE, Lyons (FR)

( * ) Notice: Subject to any disclaimer, the term of this patent is extended or adjusted under 35 U.S.C. 154(b) by 0 days.

(21) Appl. No.: 16/492,218

(22) PCT Filed: Mar. 6, 2018

(86) PCT No.: PCT/FR2018/050499
§ 371 (c)(1),
(2) Date: Sep. 9, 2019

(87) PCT Pub. No.: WO2018/162830
PCT Pub. Date: Sep. 13, 2018

(65) Prior Publication Data
US 2020/0000754 A1 Jan. 2, 2020

(30) Foreign Application Priority Data
Mar. 7, 2017 (FR) ...................................... 17/51823

(51) Int. Cl.
| | | |
|---|---|---|
| *A61K 31/195* | (2006.01) | |
| *A61K 9/00* | (2006.01) | |
| *A61K 9/08* | (2006.01) | |
| *A61K 31/728* | (2006.01) | |
| *A61K 31/23* | (2006.01) | |
| *A61K 31/34* | (2006.01) | |
| *A61K 31/22* | (2006.01) | |

(52) U.S. Cl.
CPC .......... *A61K 31/195* (2013.01); *A61K 9/0019* (2013.01); *A61K 9/08* (2013.01); *A61K 31/22* (2013.01); *A61K 31/23* (2013.01); *A61K 31/34* (2013.01); *A61K 31/728* (2013.01)

(58) Field of Classification Search
CPC .. A61K 9/0014; A61K 9/0019; A61K 31/195; A61K 31/728; A61K 38/01–04; A61K 38/12; A61K 31/722; A61K 31/723; A61K 31/726; A61K 31/727; A61K 31/731; A61K 31/734; A61P 17/00–02; A61P 19/00–02
See application file for complete search history.

(56) References Cited

U.S. PATENT DOCUMENTS

| | | | |
|---|---|---|---|
| 6,186,148 B1 * | 2/2001 | Okada | ................... A61F 2/1613 128/898 |
| 2010/0184720 A1 | 7/2010 | Gavard Molliard et al. | |
| 2013/0018020 A1 * | 1/2013 | Shin | ....................... A61Q 19/00 514/161 |
| 2014/0088039 A1 | 3/2014 | Inagaki et al. | |

FOREIGN PATENT DOCUMENTS

| | | |
|---|---|---|
| RU | 2 128 030 C1 | 3/1999 |
| WO | 2009/024670 A2 | 2/2009 |
| WO | 2012/141536 A2 | 10/2012 |

OTHER PUBLICATIONS

Johnson, M. et al "Effectiveness of sodium hyaluronate eyedrops . . . " Graefe's Arch. Clin. Exp. Ophthalmol., vol. 244, pp. 109-112. (Year: 2006).*
Salzillo, R. et al "Optimization of hyaluronan-based eye drop formulations" Carbohyd. Polym., vol. 153, pp. 275-283. (Year: 2016).*
Bhuanatanondh, P. et al "Rheology ofosteoarthritic synovial fluid . . . " Biomed. Eng. Lett., vol. 1, pp. 213-219. (Year: 2011).*
Ong, K. et al "Hyaluronic acid injections in medicare knee osteoarthritis . . . " J. Arthroplasty, vol. 31, pp. 1667-1673. (Year: 2016).*
Ishida, K. et al "Intra-articular injection of tranexamic acid . . . " Int. Orthopaed., vol. 35, pp. 1639-1645. (Year: 2011).*
Jun. 19, 2018 Written Opinion of the International Searching Authority issued in International Patent Application No. PCT/FR2018/050499.
Jun. 19, 2018 International Search Report issued in International Patent Application No. PCT/FR2018/050499.
Apr. 7, 2021 Office Action issued in Eurasian Patent Application No. 201992048/28.

* cited by examiner

*Primary Examiner* — Leigh C Maier
(74) *Attorney, Agent, or Firm* — Oliff PLC

(57) ABSTRACT

A viscoelastic solution including a polysaccharide selected from hyaluronic acid, chondroitin sulfate, keratan, keratan sulfate, dermatan sulfate, heparin, heparan sulfate, chitosan, xanthans, alginates and carrageenans, or one of the salts thereof; and an antifibrinolytic agent selected from tranexamic acid, epsilon-aminocaproic acid, protamine and desmopressin; and its use in rheumatology.

10 Claims, 1 Drawing Sheet

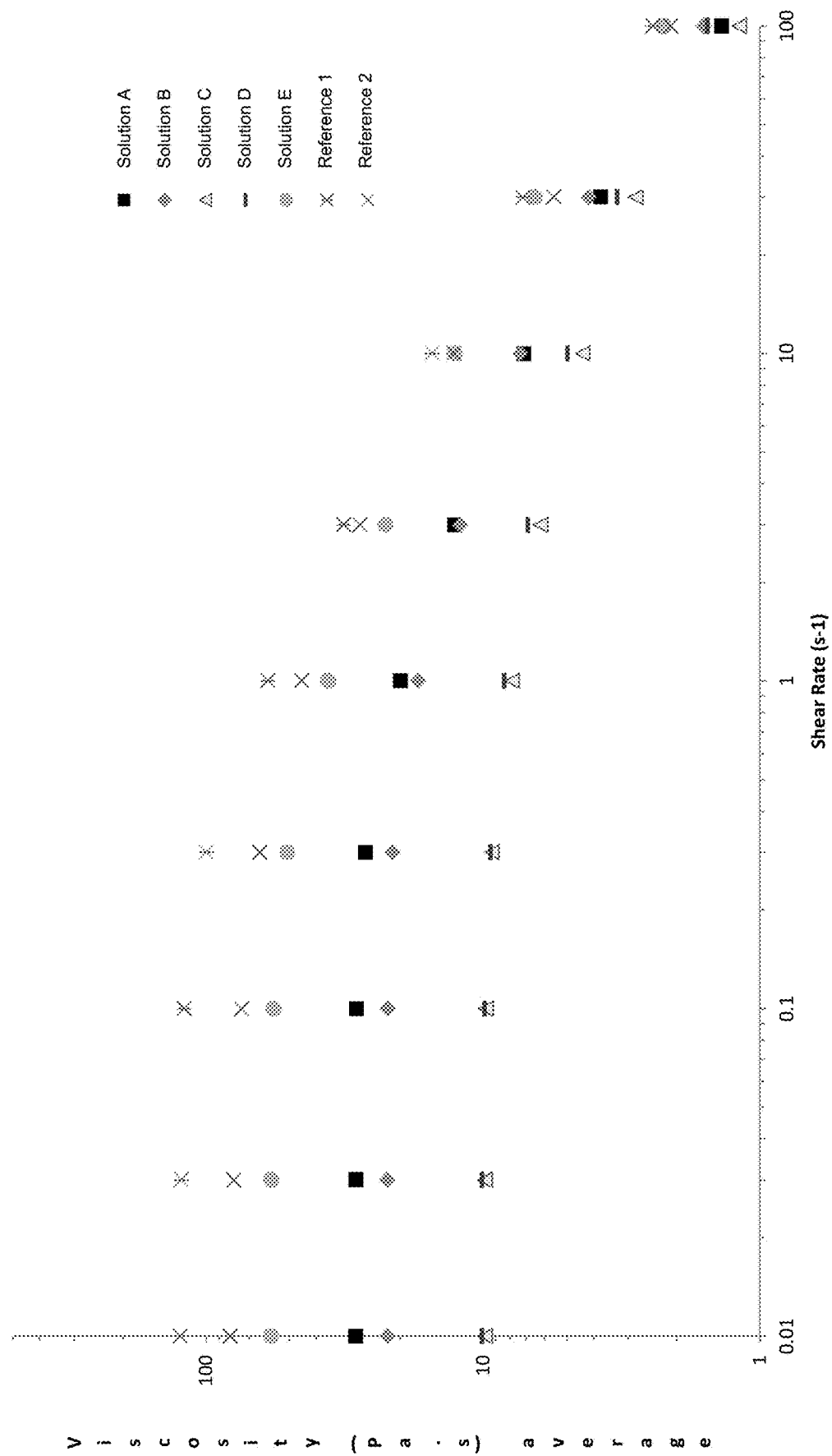
Figure 1 – Viscosity of the solutions as a function of the shear rate

VISCOELASTIC SOLUTION AND USE THEREOF IN RHUMATOLOGY

The present invention relates to a viscoelastic solution comprising a polysaccharide and an antifibrinolytic agent, and the use of this solution in rheumatology.

A joint, in anatomy, corresponds to the structure which allows connecting two bones and giving them a mobility relative to each other. Besides the two bones that compose it, a joint is constituted by the hyaline cartilage which covers the bone surfaces, a synovial membrane lining a fibrous capsule, all being stabilized by a muscular-ligamentous system. A diarthrodial joint is characterized by the presence of synovia, a biological fluid produced by the synovial membrane, which facilitates the movement, absorbs the shocks and protects the articular cartilage from erosion.

The synovial fluid is a plasma dialysate composed of electrolytes, glucose, proteins, glycoproteins and hyaluronic acid. The hyaluronic acid is synthesized in situ by two types of cells: synoviocytes and chondrocytes. It is the hyaluronic acid that confers to the synovial fluid its viscoelastic properties, essential for the proper operation of the joint.

Osteoarthritis is a degenerative joint disease related to a progressive degradation of the cartilaginous matrix which occurs depending on multiple factors, the main ones being the age, the excess of mechanical stresses (overweight, trauma, axis defect), some metabolic factors (metabolic syndrome, type II diabetes, obesity) and the genetic predisposition.

In case of osteoarthritis or in response to abnormal mechanical overloads, the cartilage undergoes early transformations that chondrocytes try to repair by the growth factor synthesis, including TGF β and IGF1. Activated chondrocytes secrete, in parallel, large amounts of proteases, matrix metalloproteases (also referred to as MMPs), into the cartilage causing the cartilage degradation. This results in a deregulation of the plasminogen/plasmin system which further stimulates the production of MMPs, thus creating the «vicious circle» of the degradation.

The main symptom of osteoarthritis is pain. To relieve this pain, intra-articular injection of corticosteroids has been used in particular for more than sixty years. Nevertheless, if these injections allow relieving joint inflammatory pains, their effectiveness is of short duration and they cannot be repeated beyond three or four times a year, in particular because of the associated adverse effects.

Therefore, researches have been conducted in order to identify alternative treatments allowing effectively relieving pain while limiting the discomforts associated with the use of corticosteroids. In the context of these researches, treatments called «viscosupplementation» treatments based on hyaluronic acid have been identified. The viscosupplementation consists in injecting a viscoelastic solution, generally containing hyaluronic acid, into the osteoarthritic joint in order to lubricate the joint and limit the friction phenomena and therefore the pain associated with the cartilaginous degradation. Indeed, during the osteoarthritis of the knee, there has been a very significant decrease of hyaluronic acid of the synovial fluid, both qualitative and quantitative, with regards to the healthy synovial fluid. Hyaluronic acid forms with water a viscoelastic deformable gel which contributes to the lubrication of the joint and to the proper operation of the cartilage and the ligamentocapsular structures.

Two generations of «viscosupplements» have thus emerged since the end of the 1960s:
the viscosupplements called «first generation» viscosupplements consist only of hyaluronic acid and differ from each other only in characteristics such as the molecular weight, the concentration, the structure (linear or crosslinked) or the volume. These linear products with a molecular weight ranging from $0.7 \times 10^6$ Da to $2 \times 10^6$ Da after sterilization, with a variable concentration ranging from 0.8 to 2.5%, have viscoelastic properties directly proportional to their concentration and to their molecular weight. The crosslinked products are differentiated by the type of crosslinking, the concentration and the volume to be injected; and the viscosupplements called «second generation» viscosupplements associate a hyaluronic acid solution with a polyol (mannitol or sorbitol) which, by protecting the hyaluronic acid molecule from degradation, aims at improving the performances of viscosupplementation.

Although hyaluronic acid is now widely used in rheumatology, the effectiveness of the products still needs to be improved. Indeed, problems of stability and durability of the hyaluronic acid solutions injected into the joint limit their lubricating effect over time. It is therefore necessary, to effectively relieve the pain of the patient with osteoarthritis, to perform very frequent intra-articular injections. It is therefore crucial, in order to improve the comfort of the patients with osteoarthritis, to extend the stability, and therefore the stay time in the joint, of the viscosupplements used in the viscosupplementation treatments.

Yet, it has now been found, quite surprisingly, that the addition of some antifibrinolytic agents such as tranexamic acid allows significantly improving the stability of the viscosupplements in the joint and to significantly extend their lubricating effect over time.

Thus, the present invention relates to a viscoelastic solution comprising:
a polysaccharide selected from hyaluronic acid, chondroitin sulfate, keratan, keratan sulfate, dermatan sulfate, heparin, heparan sulfate, chitosan, xanthan, alginates and carrageenans, or one of the salts thereof; and
an antifibrinolytic agent selected from tranexamic acid, epsilon-aminocaproic acid, protamine and desmopressin.

The viscoelastic solutions according to the present invention may be used as viscosupplements and have a significantly improved stability in the joint compared to the conventionally used viscosupplements. Their lubricating effect is therefore substantially extended over time.

In the context of the present invention:
the term «viscoelastic solution» refers to any solution having rheological properties (viscosity and elasticity) comparable to or greater than that of a healthy synovial fluid. The viscosity of a solution may in particular be measured at 6 different shear rates on the conical plate viscometer to assess the non-Newtonian behavior of the fluid. The (linear) elasticity of a solution may in turn be measured by a low amplitude oscillatory shear strength test during which, the response of the deformation to a small sinusoidal shear stress is measured for 10 frequencies comprises between 100 and 0.1 Hz;
the term «viscosupplements» refers to any injectable viscoelastic solution in an osteoarthritic joint in order to lubricate said joint and limit the friction phenomena and therefore the pain associated with the cartilaginous degradation;
the term «tranexamic acid» refers to tranexamic acid in its three forms, namely the synthetic derivative of lysine with a carboxylic acid function and an amine function branched at 1,4 (para) on a cyclohexane, the BOC-tranexamic acid derivative (protection of the amine function by tert-butoxycarbonyl) and the FMOC-tranexamic acid derivative (protection of the amine function by fluorenylmethoxycarbonyl);

the term «xanthan» refers to any polysaccharide obtained by bacterial fermentation of formula $C_{35}H_{49}O_{29}$ whose structure is a pentasaccharide assembly consisting of the combination of glucose, mannose units and derivatives of these molecules;

the term «alginates» refers to any water-soluble salt of alginic acid with alkali metals such as sodium (also referred to as sodium alginate), potassium, lithium, lower amine and substituted ammonium cations such as methylamine, ethanolamine, diethanolamine, triethanolamine;

the term «carrageenans» refers to any sulphated linear polysaccharide extracted from red algae, whose chemical structure is represented by a chain of galactose and anhydro-galactose molecules forming disaccharide patterns or D-galactopyranoses; and the term «salt» refers to any addition salt with a mineral or organic acid by action of such an acid within an organic or aqueous solvent such as an alcohol, a ketone, an ether or a chlorinated solvent, and which is acceptable from a pharmaceutical point of view. As example of such salts, the following salts may be mentioned: benzenesulphonate, hydrobromide, hydrochloride, citrate, ethanesulfonate, fumarate, gluconate, iodate, isethionate, maleate, methanesulphonate, methylene-bis-b-oxynaphthoate, nitrate, oxalate, palmoate, phosphate, salicylate, sulfate, tartrate, theophyllinacetate and p-toluenesulfonate.

The viscoelastic solution according to the present invention therefore contains a polysaccharide and an antifibrinolytic agent as previously defined. Preferably, the present invention relates to a viscoelastic solution having the following characteristics, considered alone or in combination:

the polysaccharide is selected as being hyaluronic acid or one of the salts thereof. Preferably, the polysaccharide is selected as being hyaluronic acid, sodium hyaluronate or zinc hyaluronate. More preferably, the polysaccharide is selected as being sodium hyaluronate;

the molecular mass of the polysaccharide varies from 10 to 4500 kDa; preferably from 500 to 4000 kDa; more preferably from 3000 to 3500 kDa;

the solution contains from 0.1 to 100 mg/ml of polysaccharide; preferably from 1 to 70 mg/ml of polysaccharide; more preferably from 10 to 30 mg/ml of polysaccharide;

the antifibrinolytic agent is selected as being tranexamic acid; and/or the solution contains from 0.1 to 100 mg/ml of antifibrinolytic agent;

preferably from 1 to 70 mg/ml of antifibrinolytic agent; more preferably from 10 to 50 mg/ml of an antifibrinolytic agent.

As examples of viscoelastic solutions according to the invention, mention may be made in particular to:

a viscoelastic solution comprising a polysaccharide selected as being hyaluronic acid and an antifibrinolytic agent selected as being tranexamic acid;

a viscoelastic solution comprising a polysaccharide selected as being hyaluronic acid and an antifibrinolytic agent selected as being epsilon-aminocaproic acid;

a viscoelastic solution comprising a polysaccharide selected as being hyaluronic acid and an antifibrinolytic agent selected as being protamine;

a viscoelastic solution comprising a polysaccharide selected as being hyaluronic acid and an antifibrinolytic agent selected as being desmopressin;

a viscoelastic solution comprising a polysaccharide selected as being chondroitin sulfate and an antifibrinolytic agent selected as being tranexamic acid;

a viscoelastic solution comprising a polysaccharide selected as being chondroitin sulfate and an antifibrinolytic agent selected as being epsilon-aminocaproic acid;

a viscoelastic solution comprising a polysaccharide selected as being chondroitin sulfate and an antifibrinolytic agent selected as being protamine;

a viscoelastic solution comprising a polysaccharide selected as being chondroitin sulfate and an antifibrinolytic agent selected as being desmopressin;

a viscoelastic solution comprising a polysaccharide selected as being keratan and an antifibrinolytic agent selected as being tranexamic acid;

a viscoelastic solution comprising a polysaccharide selected as being keratane and an antifibrinolytic agent selected as being epsilon-aminocaproic acid;

a viscoelastic solution comprising a polysaccharide selected as being keratan and an antifibrinolytic agent selected as being protamine;

a viscoelastic solution comprising a polysaccharide selected as being keratan and an antifibrinolytic agent selected as being desmopressin;

a viscoelastic solution comprising a polysaccharide selected as being keratan sulfate and an antifibrinolytic agent selected as being tranexamic acid;

a viscoelastic solution comprising a polysaccharide selected as being keratan sulfate and an antifibrinolytic agent selected as being epsilon-aminocaproic acid;

a viscoelastic solution comprising a polysaccharide selected as being keratan sulfate and an antifibrinolytic agent selected as being protamine;

a viscoelastic solution comprising a polysaccharide selected as being keratan sulfate and an antifibrinolytic agent selected as being desmopressin;

a viscoelastic solution comprising a polysaccharide selected as being dermatan sulfate and an antifibrinolytic agent selected as being tranexamic acid;

a viscoelastic solution comprising a polysaccharide selected as being dermatan sulfate and an antifibrinolytic agent selected as being epsilon-aminocaproic acid;

a viscoelastic solution comprising a polysaccharide selected as being dermatan sulfate and an antifibrinolytic agent selected as being protamine;

a viscoelastic solution comprising a polysaccharide selected as being dermatan sulfate and an antifibrinolytic agent selected as being desmopressin;

a viscoelastic solution comprising a polysaccharide selected as being heparin and an antifibrinolytic agent selected as being tranexamic acid;

a viscoelastic solution comprising a polysaccharide selected as being heparin and an antifibrinolytic agent selected as being epsilon-aminocaproic acid;

a viscoelastic solution comprising a polysaccharide selected as being heparin and an antifibrinolytic agent selected as being protamine;

a viscoelastic solution comprising a polysaccharide selected as being heparin and an antifibrinolytic agent selected as being desmopressin;

- a viscoelastic solution comprising a polysaccharide selected as being heparan sulfate and an antifibrinolytic agent selected as being tranexamic acid;
- a viscoelastic solution comprising a polysaccharide selected as being heparan sulfate and an antifibrinolytic agent selected as being epsilon-aminocaproic acid;
- a viscoelastic solution comprising a polysaccharide selected as being heparan sulfate and an antifibrinolytic agent selected as being protamine;
- a viscoelastic solution comprising a polysaccharide selected as being heparan sulfate and an antifibrinolytic agent selected as being desmopressin;
- a viscoelastic solution comprising a polysaccharide selected as being chitosan and an antifibrinolytic agent selected as being tranexamic acid;
- a viscoelastic solution comprising a polysaccharide selected as being chitosan and an antifibrinolytic agent selected as being epsilon-aminocaproic acid;
- a viscoelastic solution comprising a polysaccharide selected as being chitosan and an antifibrinolytic agent selected as being protamine;
- a viscoelastic solution comprising a polysaccharide selected as being chitosan and an antifibrinolytic agent selected as being desmopressin;
- a viscoelastic solution comprising a polysaccharide selected as being xanthan and an antifibrinolytic agent selected as being tranexamic acid;
- a viscoelastic solution comprising a polysaccharide selected as being xanthan and an antifibrinolytic agent selected as being epsilon-aminocaproic acid;
- a viscoelastic solution comprising a polysaccharide selected as being xanthan and an antifibrinolytic agent selected as being protamine;
- a viscoelastic solution comprising a polysaccharide selected as being xanthan and an antifibrinolytic agent selected as being desmopressin;
- a viscoelastic solution comprising a polysaccharide selected as being alginates and an antifibrinolytic agent selected as being tranexamic acid;
- a viscoelastic solution comprising a polysaccharide selected as being alginates and an antifibrinolytic agent selected as being epsilon-aminocaproic acid;
- a viscoelastic solution comprising a polysaccharide selected as being alginates and an antifibrinolytic agent selected as being protamine;
- a viscoelastic solution comprising a polysaccharide selected as being alginates and an antifibrinolytic agent selected as being desmopressin;
- a viscoelastic solution comprising a polysaccharide selected as being carrageenans and an antifibrinolytic agent selected as being tranexamic acid;
- a viscoelastic solution comprising a polysaccharide selected as being carrageenans and an antifibrinolytic agent selected as being epsilon-aminocaproic acid;
- a viscoelastic solution comprising a polysaccharide selected as being carrageenans and an antifibrinolytic agent selected as being protamine; or
- a viscoelastic solution comprising a polysaccharide selected as being carrageenans and an antifibrinolytic agent selected as being desmopressin.

The viscoelastic solution may further contain a polyol, which further allows improving the protection of hyaluronic acid against degradation in the joint. Thus, the present invention also relates to a viscoelastic solution as previously defined, said solution further containing a polyol.

Preferably, said polyol is selected as being glycerol, propylene glycol, sorbitol, mannitol or xylitol. More preferably, the polyol is selected as being mannitol or sorbitol. Preferably, the solution according to the present invention contains from 0.1 to 100 mg/ml of polyol, preferably from 1 to 70 mg/ml of polyol, more preferably from 5 to 50 mg/ml of polyol.

The viscoelastic solution according to the present invention is administered intra-articularly. To do so, the solution may be in any form adapted to such an administration. Preferably, the solution according to the present invention is contained in a glass or plastic polymer vial of 0.1 to 20 ml. More preferably, the solution is contained in a ready-to-use syringe.

The viscoelastic solution according to the present invention is administered in variable volumes depending on the concerned joint and the progress of its deterioration. Preferably, the solution according to the present invention is administered in volumes ranging from 0.1 ml to 10 ml.

The viscoelastic solution according to the present invention may be administered according to a continuous schedule or not and at any time of the day. Preferably, the solution according to the present invention is administered every seven to twenty-eight days, more preferably every seven days. The treatment duration will be refined depending on the patient and the intensity of the symptoms.

The viscoelastic solution according to the present invention may therefore be used as a viscosupplement. Thus, the present invention also relates to the use of a viscoelastic solution as previously defined as a viscosupplement.

Given the properties of the viscoelastic solution according to the present invention, other uses thereof may also be considered. Thus, the viscoelastic solution according to the present invention may also be used.
- in aesthetic medicine for filling wrinkles and furrows;
- in ophthalmology for the protection, the lubrication or the support of cells or tissues during surgical procedures on the eye such as, for example, the surgery of the cataract or the glaucoma, the corneal transplants or, the intraocular implants placement; or
- in urology/gynecology as a gel allowing, for example, increasing the volume of the sphincter or the urethra, lubricating the vaginal walls or reducing the cell/tissue adherences.

The present invention is illustrated in a non-limiting manner by the following examples.

EXAMPLE 1

Preparation of a Viscoelastic Solution According to the Invention

The following method allows preparing the viscoelastic solutions A to E whose composition is reported in Tables 1 to 5 below.

A solution of 125 ml of phosphate buffer is prepared, whose pH varies between 7.0 and 7.3, and whose osmolarity is adjusted to 260 to 320 mOsm/kg by addition of NaCl salt. The desired amount of tranexamic acid and then of hyaluronic acid are added to this buffer solution and mixed until a homogeneous viscous solution is obtained.

TABLE 1

| Viscoelastic Solution A | |
| --- | --- |
| Ingredient | Quantity (in mg/ml) |
| Sodium Hyaluronate | 18 |
| Tranexamic acid | 10 |

TABLE 2

Viscoelastic Solution B

| Ingredient | Quantity (in mg/ml) |
| --- | --- |
| Sodium Hyaluronate | 18 |
| Tranexamic acid | 20 |

TABLE 3

Viscoelastic Solution C

| Ingredient | Quantity (in mg/ml) |
| --- | --- |
| Sodium Hyaluronate | 18 |
| Tranexamic acid | 30 |

TABLE 4

Viscoelastic Solution D

| Ingredient | Quantity (in mg/ml) |
| --- | --- |
| Sodium Hyaluronate | 18 |
| Tranexamic acid | 40 |

TABLE 5

Viscoelastic Solution E

| Ingredient | Quantity (in mg/ml) |
| --- | --- |
| Sodium Hyaluronate | 22 |
| Tranexamic acid | 15 |

EXAMPLE 2

Resistance to Degradation of the Solutions of the Invention

The resistance to degradation by hyaluronidase over time of a viscoelastic solution according to the invention (solution E—Table 5) is compared with a reference viscoelastic solution without tranexamic acid (Reference 1—Table 6).

TABLE 6

Conventional Viscoelastic Solution (Reference 1)

| Ingredient | Quantity (in mg/ml) |
| --- | --- |
| Sodium Hyaluronate | 22 |
| Tranexamic acid | 0 |

To do so, the evolution of the viscosity of the two viscoelastic solutions over time is measured according to the following protocol:

5.8 mg of enzyme (hyaluronidase Sigma from sheep type testes, Type III, lyophilized powder, ≥500 U/mg) are dissolved in 5 ml of phosphate buffer PBS pH=7.3 (DPBS Tampon Gibco by Life Technologies). the kinetics of degradation of the hyaluronic acid in the solution E and in the reference solution 1 are measured by measuring the viscosity at $1\ s^{-1}$.

The tests were carried out with 5 µl of enzymatic solution for 3 ml of solution E or of Reference 1.

The slope of the enzymatic degradation curve after addition of 5 µl of hyaluronidase has thus been measured. The results are reported in the following Table 7:

TABLE 7

Slope of the enzymatic degradation curve after addition of hyaluronidase

|  | Test 1 | Test 2 |
| --- | --- | --- |
| Reference 1 | 0.019 | 0.015 |
| Solution E | 0.0041 | 0.0042 |

As shown in the previous results, the degradation slope of hyaluronic acid is three times lower in the presence of tranexamic acid 15 mg/ml (average: 0.0042 versus 0.015). This indicates that tranexamic acid protects hyaluronic acid effectively against degradations by hyaluronidase and increases the stay time and the stability of hyaluronic acid. The solution according to the present invention (formulation E). The solution according to the present invention is therefore much more stable and effective over time than conventionally used solutions.

The invention claimed is:

1. A viscosupplement solution that is viscoelastic comprising:
   from 0.1 to 100 mg/ml of a polysaccharide selected from hyaluronic acid, chitosan, xanthan, alginates and carrageenans, or one of the salts thereof; and
   from 0.1 to 100 mg/ml of an antifibrinolytic agent selected from tranexamic acid, epsilon-aminocaproic acid, protamine and desmopressin.

2. The solution according to claim 1, wherein the polysaccharide is chosen as being hyaluronic acid or one of the salts thereof.

3. The solution according to claim 1, wherein the solution contains from 10 to 30 mg/ml of the polysaccharide.

4. The solution according to claim 1, wherein the antifibrinolytic agent is tranexamic acid.

5. The solution according to claim 1, wherein the solution contains from 10 to 50 mg/ml of the antifibrinolytic agent.

6. The solution according to claim 1, wherein the solution further contains a polyol chosen as being glycerol, propylene glycol, sorbitol, mannitol or xylitol.

7. The solution according to claim 6, wherein the solution contains from 0.1 to 100 mg/ml of the polyol.

8. A method comprising intra-articular injection of a solution according to claim 1 as a viscosupplement to a subject in need of the viscosupplement.

9. The solution according to claim 1, wherein the polysaccharide is chosen as being hyaluronic acid or one of the salts thereof, and the antifibrinolytic agent is chosen as being tranexamic acid.

10. The solution according to claim 1, wherein the solution further comprises one or more of chondroitin sulfate, keratan, keratan sulfate, dermatan sulfate, heparin or heparan sulfate.

* * * * *